US008535878B2

(12) United States Patent
Ruff et al.

(10) Patent No.: US 8,535,878 B2
(45) Date of Patent: Sep. 17, 2013

(54) METHODS, COMPOSITIONS, AND KITS FOR DETECTING PROTEIN AGGREGATES

(75) Inventors: David W. Ruff, San Francisco, CA (US); Mark E. Shannon, San Francisco, CA (US); Kenneth J. Livak, San Jose, CA (US); Karl J. Guegler, Menlo Park, CA (US); Kevin M. Hennessy, San Mateo, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 397 days.

(21) Appl. No.: 11/743,517

(22) Filed: May 2, 2007

(65) Prior Publication Data
US 2008/0003604 A1 Jan. 3, 2008

Related U.S. Application Data

(60) Provisional application No. 60/797,460, filed on May 3, 2006.

(51) Int. Cl.
*C12Q 1/68* (2006.01)

(52) U.S. Cl.
USPC .......... 435/6.1; 435/6.11; 435/6.12; 435/6.15

(58) Field of Classification Search
None
See application file for complete search history.

(56) References Cited

U.S. PATENT DOCUMENTS

| | | | |
|---|---|---|---|
| 4,774,175 A | 9/1988 | Chang | |
| 5,739,042 A | 4/1998 | Frengen | |
| 6,783,934 B1 * | 8/2004 | McMillan et al. | 435/6 |
| 6,846,640 B2 * | 1/2005 | Peach et al. | 435/7.1 |
| 7,306,904 B2 * | 12/2007 | Landegren et al. | 435/6 |
| 2002/0064779 A1 * | 5/2002 | Landegren et al. | 435/6 |
| 2004/0038200 A1 | 2/2004 | Wilson et al. | |
| 2005/0003361 A1 | 1/2005 | Fredriksson | |
| 2006/0064779 A1 | 3/2006 | Liebergesell | |
| 2007/0026430 A1 | 2/2007 | Andersen et al. | |

FOREIGN PATENT DOCUMENTS

| | | | |
|---|---|---|---|
| WO | WO9929891 | * | 6/1999 |
| WO | WO-0138354 | | 5/2001 |
| WO | WO-0204954 | | 1/2002 |
| WO | WO-2007/107743 | | 9/2007 |
| WO | W-20070128004 | | 11/2007 |

OTHER PUBLICATIONS

Berthelier et al., "A Microtiter Plate Assay for Polyglutamine Aggregate Extension," Anal. Biochem., 2001, vol. 295, issue 2, pp. 227-236.*
Perutz et al., "Aggregation of proteins with expanded glutamine and alanine repeats of the glutamine-rich and asparagine-rich domains of Sup35 and of the amyloid β-peptide of amyloid plaques," PNAS, 2002, vol. 99, No. 8, pp. 5596-5600.*
Fredriksson et al., "Protein Detection Using Proximity Dependent DNA Ligation Assays", Nature Biotechnology, 2002, 20, 473-477.
Gullberg et al., "A sense of closeness: protein detection by proximity ligation", Current Opin. Biotechnol, 2003, vol. 14 No. 1, pp. 82-86.
Gullberg et al., "Cytokine detection by antibody-based proximity ligation", Proc. Nat. Acad. Sci. U.S.A., 2004, vol. 101 No. 22, pp. 8420-8424.
International Search Report for application No. PCT/US2007/68046, Mailed on Oct. 27, 2008, 2 pages.
Pai et al., "Proximity ligation assays with peptide conjugate 'burrs' for the sensitive detection of spores", Nucleic Acids Research, 2005, vol. 33 No. 18, pp. e162.
07783116.2, "Extended European Search Report mailed May, 18, 2010", 11.
Schallmeiner, E. et al., "Sensitive Protein Detection Via Triple-Binder Proximity Ligation Assays", *Nature Methods, Nature Publishing Group*,GB LNKD-DOI:10.1038/NMETH974, vol. 4, No. 2, pp. 135-137 (Feb. 2001).
Aguzzi, Adriano et al., "Mammalian Prion Biology: One Century of Evolving Concepts", *Cell* vol. 116, Jan. 23, 2004, 313-327.
Arora, Anubhav et al., "Inhibition of Insulin Amyloid Formation by Small Stress Molecules", *FEBS Letters*, vol. 564, 2004, 121-125.
Balbirnie, Melinda et al., "An Amyloid-Forming Peptide from the Yeast Prion Sup35 Reveals a Dehydrated B-sheet Structure for Amyloid", *PNAS*, vol. 98, No. 5, Feb. 27, 2001, 2375-2380.
Castilla, Joaquin et al., "Detection of Prions in Blood", *Nature Medicine* vol. 11, No. 9, Sep. 2005, 982-985.
Michelitsch, Melissa D., et al., "A Census of Glutamine/Asparagine-rich Regions: Implications for Their Conserved Function and the Prediction of Novel Prions", *Proc Natl Acad Sci*, (PNAS), vol. 97, No. 22, Oct. 24, 2000, 11910-11915.
Narayanan, Saravanakumar et al., "Yeast Prion-Protein, Sup35, Fibril formation Proceeds by Addition and Substraction of Oligomers", *Chem Bio Chem*, vol. 7, 2006, 757-765.
Pai, Supriya et al., "Proximity Litigation Assays with Peptide Conjugate 'Burrs' for the Sensitive Detection of Spores", *Nucleic Acids Research*, vol. 33, No. 18, Oct. 19, 2005, e162.
PCT/US07/68046 International Preliminary Report on Patentability Oct. 27, 2008.
PCT/US07/68046 Written Opinion Mailed Oct. 27, 2008.
Ross, Eric D., et al., "Prion Domains: Sequences, Structures and Interactions", *Nature Cell Biology*, vol. 7, No. 11, Nov. 2005, 1039-1044.
Saa, Paula et al., "Cyclic Amplification of Protein Misfolding and Aggregation", *Methods in Molecular Biology*, vol. 299; Amloid Proteins: Methods and Protocols Edited by: E.M. Sigurdsson, Humana Press Inc., Totowa, NJ 2005, 53-65.

(Continued)

*Primary Examiner* — Shafiqul Haq
*Assistant Examiner* — Galina Yakovleva

(57) ABSTRACT

The present teachings provide methods, compositions, and kits for detecting the presence of protein aggregates. In some embodiments, the protein aggregate is treated with a labeled precursor, and the labeled precursor is incorporated into the protein aggregate to form a labeled protein aggregate. The labeled protein aggregate is then measured, thus detecting the presence of the protein aggregate. In some embodiments, the labeled protein aggregate is detected by interaction of labeled precursors, for example by a proximity ligation assay.

4 Claims, 9 Drawing Sheets

(56) References Cited

OTHER PUBLICATIONS

Si, Kausik et al., "A Neuronal Isoform of CPEB Regulates Local Protein Synthesis and Stabilizes Synapse-Specific Long-Term Facilitation in Aplysia", *Cell* vol. 115, Dec. 26, 2003, 893-904.

Si, Kausik et al,, "A Neuronal Isoforrn of the Aplysia CPEB Has Prion-Like Properties", *Cell* vol. 115, Dec. 26, 2003, 879-891.

Wickner, R. B., et al., "Prions of Yeast are Genes Made of Protein: Amyloids and Enzymes", *Cold Spring Harbor Symposium on Quantitative Biology*, vol. 69, 2004, 489-496.

\* cited by examiner

SEQUENCE LISTING

<160> NUMBER OF SEQ ID NOS: 4

<210> SEQ ID NO 1
<211> LENGTH: 26
<212> TYPE: DNA
<213> ORGANISM: Saccharomyces cerevisiae -continued

```
<400> SEQUENCE: 1
cttcatcgac ttgctcggaa taacat                                          26

<210> SEQ ID NO 2
<211> LENGTH: 27
<212> TYPE: DNA
<213> ORGANISM: Saccharomyces cerevisiae

<400> SEQUENCE: 2
ggaagggtta tgatgaaaac gtgattg                                         27

<210> SEQ ID NO 3
<211> LENGTH: 32
<212> TYPE: DNA
<213> ORGANISM: Saccharomyces cerevisiae

<400> SEQUENCE: 3
gcggatccat gtcggattca aaccaaggca ac                                   32

<210> SEQ ID NO 4
<211> LENGTH: 33
<212> TYPE: DNA
<213> ORGANISM: Saccharomyces cerevisiae

<400> SEQUENCE: 4
gcctcgagct cggcaatttt aacaatttta cca                                  33
```

METHODS, COMPOSITIONS, AND KITS FOR DETECTING PROTEIN AGGREGATES

CROSS-REFERENCE TO RELATED APPLICATIONS

This application claims a priority benefit under 35 U.S.C. §119(e) from U.S. Application No. 60/797,460,filed May 3, 2006, the contents of which are incorporated herein by reference.

FIELD

The present teachings relate to methods, compositions, and kits for detecting protein aggregates.

INTRODUCTION

Self-assembling macromolecules are found throughout nature and are essential for normal cellular function. All classes of macromolecules, including nucleic acids, proteins, lipids and carbohydrates, are capable of higher order self-assembly. Proteins are capable of forming a diverse array of macromolecular complexes exemplified by actin/myosin filaments, cytoskeletal structures such as spectrin/ankyrin, and multimeric homo- and hetero- proteins such as TNF-alpha, PDGF, histones and transcription factor complexes at gene promoters (multi-protein/DNA assemblages). In addition to the normal self-assembly of protein complexes, living systems are also characterized by the often-deleterious self-aggregation of abnormal or misfolded proteins. Of particular medical and diagnostic interest are the misfolded protein aggregates affiliated with neurodegenerative processes such as Alzheimer's, Huntington's, Parkinson's and mammalian prion-linked diseases (PrP scrapie related protein). See Verdile, G. et. al., Pharmacol Res. October 2004; 50(4): 397-409, Temussi, P. A. et. al., EMBO J 2003; 22(3): 355-361,Moore, R. C. et.al., Am J Hum Genet. December 2001; 69(6): 1385-8,and Stoppini, M. et.al. Pharmacol Res. October 2004; 50(4): 419-31.

There is a great need to develop assays to detect self-assembled and misfolded protein aggregates. For example, Alzheimer's, Huntington's and Parkinson's diseases are consequences of complex events occurring in aging brain tissue. Alzheimer's patients possess two major pathological abnormalities in the brain: 1) amyloid plaques and 2) neurofibrillary tangles. Amyloid plaques consist of aggregated beta amyloid protein, which is derived from a precursor, amyloid precursor protein (APP). Although APP is expressed in brain, heart, kidney, lung, spleen and intestines, its biological function is not understood. Tangles contain aggregates of the tau protein, which normally plays a role in stabilizing microtubules. There is much debate about whether these abnormal aggregate structures are the cause of the disease or simply a consequence. For instance, it is also known that other proteins are linked to the occurrence of Alzheimer's, including apolipoprotein E and presenilins, which normally process beta amyloid protein. These cellular agents, along with hereditary factors, remain targets of intense investigation into the pathology of Alzheimer's disease.

Huntington's disease is caused by the aggregation of a ~350 Kdal cytoplasmic protein called huntingtin. The normal function of huntingtin is unknown, but some evidence links its function to iron metabolic regulation and cytoskeletal structure maintenance. The outcome of self-aggregation is neuronal cell death, particularly in the basal ganglia and frontal lobes, but the mechanism of cellular toxicity is unknown. Normally, huntingtin contains fewer than 37 glutamine (Q) residues encoded in exon I. In disease patients, extra Q residues are present at the amino terminus bringing the total Q content to over 40.Apparently, the excessive Q content facilitates protein aggregation. Unlike Alzheimer's disease where hereditary contributions are not well understood, Huntington's disease has been shown to be an autosomal dominant disorder. If a person inherits the defective huntingtin gene, they will eventually develop Huntington's disease, typically after the age of 50-60.

Parkinson's disease is characterized by structural anomalies in the substantial nigra region of the brain. The afflicted cells contain proteinaceous inclusion vesicles called Lewy Bodies, composed mainly of alpha-synuclein aggregates. The normal role of alpha-synuclein is not clear; however, some evidence indicates that it interacts with p53 and protects brain cells from apoptosis. Other evidence from transgenic mouse models has shown that overexpression or reduced clearance of alpha-synuclein leads to Parkinson's-like illness. Sharply reduced levels of the neurotransmitter dopamine in the brain have also been observed for Parkinson's patients. In addition, it is thought that environmental toxin exposure may play a significant role in the development of Parkinson's disease.

In all three diseases, confirmatory diagnostic exams are based on post-mortem pathological analysis of diseased tissues. Reliable biochemical-based diagnostic tests for patients with or at risk for these diseases would therefore be quite desirable.

Prions are a particularly interesting type of aggregate. Prions are proteins that typically contain a Q/N-rich domain and can exist in two distinct conformations: an alpha-helical form, which is monomeric and soluble, and a beta-sheet, which naturally self-assembles into multimeric insoluble aggregrates. In almost all cases, the conversion of protein from the soluble monomeric alpha-helical type to the beta-sheet multimeric form is a one-way process and is essentially irreversible. The term prion (proteinaceous infectious particle) was coined by Stanley Pruisner to explain the infectious agent responsible for a distinct type of neurodegenerative disease characterized by extensive spongiform encephalopathy found in sheep (also known as scrapie), bovine (Bovine Spongiform Encephalopathy, BSE—or more widely touted as "Mad cow disease") and humans (Kuru disease, variant and spontaneous Creutzfeld-Jakob disease). There is a wide body of published literature and technical reviews on the prion research field (See for example Aguzzi, A. and Polymenidou, M., Cell 2004; 116: 313-327). Similar prion diseases have been discovered in other mammals: deer, elk and mink. Interestingly, prion proteins have also been discovered in non-mammalian organisms. Three different prion proteins have been discovered in yeast (see Wickner, R. B. et. al., CSH Symp Quant Biol. 2004; 69:489-96 and a poly-A binding prion protein in aplysia that accumulates at neuron synaptic sites (Si, K., Lindquist, S. and Kandel, E. R., Cell Dec. 26, 2003; 115(7): 879-91,and Si, K. et.al., Cell Dec. 26, 2003; 115(7): 893-904.

In yeast (*Saccharomyces cerevisiae*), there are three currently known prion proteins: Sup35,Ure2 and Rnq1.However, it is likely that many additional prion proteins will be identified in yeast—partially surmised on the surprisingly large number (107) of high Q/N content expressed genes identified through genomic analysis (Michelitsch, M. D. and Weissman, J. S., Proc Natl Acad Sci USA. Oct. 24, 2000; 97(22): 11910-15). The three proteins with known prion properties play diverse roles in the cell. Sup35 is essential for proper translation termination by the ribosome at stop codons. Ure2 regulates nitrogen catabolism by forming a transcription factor complex with Gln3 and more recently shown to play a central role in cadmium and hydrogen peroxide detoxification via its glutathione S-transferase-like domain. Rnq1 is not an essential protein for yeast survival but is thought to mediate prion conversion of the other prions.

Sup35 is composed of 685 amino acids and has a high Q/N content near the amino terminus that is essential for prion formation. It is interesting that Sup35 conformation status is mediated by molecular chaperones such as Hsp 104,Hsp70 and ubiquitin complexes. Sup35 is one of the best-characterized self-aggregating protein, and is a preferred prion model system for researchers because yeast are very amenable to biochemical manipulation by an array of molecular and cellular technologies and yeast prions do not pose an infection risk to lab personnel.

Many unique challenges impact the development of methods for the detection of prion complexes in bovine and other domesticated animals. For instance, deriving high quality antibodies is challenging because of the ubiquitous expression of prion protein in nervous and immune system tissues, conserved structural motifs amongst mammalian species and poor solubility of prion aggregates. This causes several problems with prion antibody-based detection schemes: 1) poor sensitivity 2) high false positive data output, 3) limited applicability (only to post-mortem brain tissues), 4) limited scaleability to high-throughput workflow, and thus 5) high cost (labor and materials). Consequently, there is a long-felt need for improved technologies useful for the detection of prions.

One potential approach for the detection of mammalian prions is the Protein Misfolding Cyclic Amplification process (PMCA)( See Saa, P., Castilla, J. and Soto, C., Methods Mol Biol. 2005; 299: 53-65,Castilla, J., Saa, P. and Soto, C., Nat Med. September 2005; 11 (9): 982-5,and Soto, C. and Gabriella, S. PCT publication WO0204954). This approach takes advantage of the self-assembly attributes of prions to amplify pre-existing prion particles to the extent that sufficient aggregrate material is generated to facilitate detection with antibodies or radiolabel incorporation. Most of the PMCA published data uses proteinase K digestion of the amplified product followed by western blotting for prion detection. A 30-35 Kdal proteinase K resistant prion core is detected by this method. This process uses a cyclic procedure to amplify prion aggregrates from a biological test sample. PMCA utilizes a sonication step to disrupt larger less efficient "seeding" prion aggregates into more numerous and smaller higher efficiency "seeds". Then brain homogenate from a healthy animal (containing the alpha-helical conformer of prion) is added and after a 30 minute incubation, if prion aggregrates are present, the soluble alpha-helical conformer domain is converted to beta- sheet form and incorporated into the misfolded beta-sheet aggregate. The sample is repeatedly subjected to this cyclic procedure for 144 cycles—taking some 3 days to complete.

Proximity ligation assay (PLA) is an approach for protein quantitation that can use two different binder molecules (proximity probes) to bind to a specific detection target (See for example Fredriksson, S. et al., Nat Biotechnol. 2002; 20(5): 473-77,Gullberg, M., et. al., Proc Nati Acad Sci USA. 2004; 101(22): 8420-24,Gullberg, M., et. al., Curr Opin Biotechnol. 2003; 14: 1-5,Pai, S., Ellington, A. D. and Levy, M., Nuc Acids Res. Oct. 19 2005; 33(18): e162,Landegren, U. and Fredriksson, S., US Patent Application 20020064779, May 30, 2002,Fredriksson, S., US Patent Application 20050003361). Typical binders include polyclonal or monoclonal antibody pairs. Each binder molecule can be conjugated to a specific oligonucleotide. One binder's oligonucleotide can form the "left" side of a real-time PCR amplicon, while the other binder can form the "right" side. When the two binders find and attach to the same target, the left and right oligonucleotides are brought into close proximity. With the addition of a splint oligonucleotide and ligase enzyme, the left and right oligonucleotides can become ligated and thereby allow for the formation of a complete real-time PCR amplicon. Further addition of real-time PCR reaction components (e.g. TaqMan®) followed by thermocycling generates real-time sequence detection data output. Other methods for detecting proximity of the left and right oligonucleotides include restriction digestion, and polymerase extension, as described in Published US Patent Application US20070026430.

The present teachings include new methods, reaction compositions, and kits for detecting prions and protein aggregates that improve upon and expand the applications for proximity-based assays such as PLA.

SUMMARY

In some embodiments, the present teachings provide a method of detecting a protein aggregate in a sample of interest comprising; providing a first precursor molecule and a second precursor molecule, wherein the first precursor molecule comprises a first oligonucleotide, and wherein the second precursor molecule comprises a second oligonucleotide; contacting a sample suspected of containing the protein aggregate with the first precursor molecule and the second precursor molecule;

incorporating the first precursor molecule and the second precursor molecule into the protein aggregate, if present, to form a labeled protein aggregate; interacting the first oligonucleotide of the first precursor molecule with the second oligonucleotide of the second precursor molecule, to form an interaction composition; and, measuring the interaction composition to detect the presence of the protein aggregate in the sample of interest.

In some embodiments, the present teachings provide a method of detecting a protein aggregate in a sample of interest comprising; providing a precursor molecule, wherein the precursor molecule comprises an oligonucleotide; contacting a sample suspected of containing the protein aggregate with the precursor molecule; incorporating the first precursor molecule into the protein aggregate, if present, to form a labeled aggregate protein; removing unincorporated precursor molecules; and, measuring the labeled protein aggregate to detect the presence of the protein aggregate in the sample of interest.

Additional methods, as well as reaction compositions and kits are also provided by the present teachings.

DETAILED DESCRIPTION OF VARIOUS EMBODIMENTS

Figure 1:
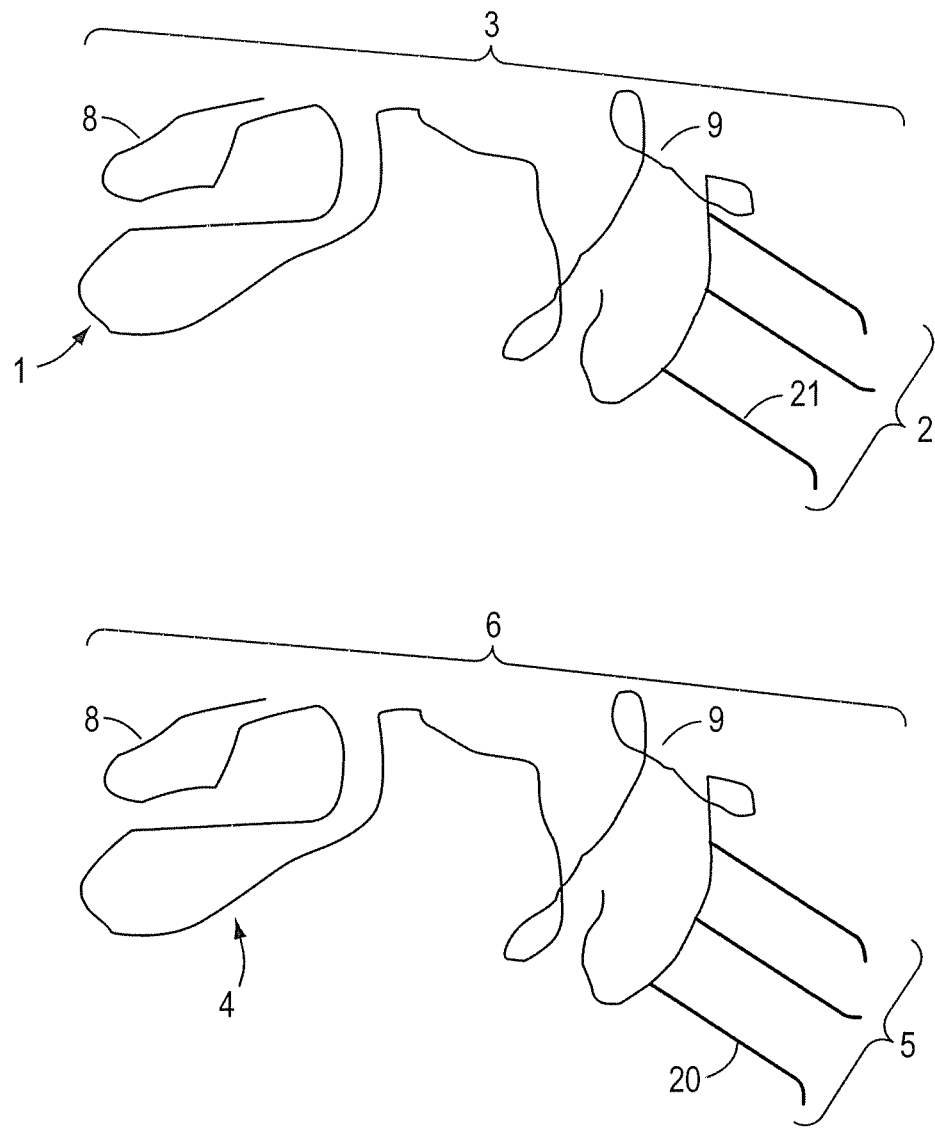
FIG. 1 depicts some embodiments of the present teachings for measuring an analyte. Here, a cartoon of the soluble precursor form of yeast Sup 35 is shown, with oligonucleotide probes attached to the C-terminal region.

In this application, the use of the singular includes the plural unless specifically stated otherwise. In this application, the word "a" or "an" means "at least one" unless specifically stated otherwise. In this application, the use of "or" means "and/or" unless stated otherwise. Furthermore, the use of the term "including," as well as other forms, such as "includes" and "included," is not limiting.

The section headings used herein are for organizational purposes only and are not to be construed as limiting the subject matter described. All documents, or portions of documents, cited in this application, including but not limited to patents, patent applications, articles, books, and treatises are hereby expressly incorporated by reference in their entirety for any purpose. In the event that one or more of the incorporated documents defines a term that contradicts that term's definition in this application, this application controls.

As used herein, the term "soluble precursor molecule" refers to a correctly folded protein that is not yet in the conformation present in a protein aggregate.

As used herein, the term "left oligonucleotide" refers to an oligonucleotide which can be present on a soluble precursor molecule, and is generally of a different nucleotide sequence than a right oligonucleotide.

As used herein, the term "right oligonucleotide" refers to an oligonucleotide which can be present on a soluble precursor molecule, and is generally of a different nucleotide sequence than a left oligonucleotide.

As used herein, the term "labeled precursor" refers to a correctly folded protein that is not in the conformation present in a protein aggregate, which contains a label such an oligonucleotide, fluorophore, etc.

As used herein, the term "protein aggregate" refers to a collection of proteins that are mis-folded and grouped together. Generally, the proteins in a protein aggregate can be, prior to their aggregation, soluble precursors.

As used herein, the term "labeled protein aggregate" refers to a collection of proteins that are mis-folded and grouped together, and that furthermore contain at least one protein that was, prior to its incorporation in the aggregate, a labeled precursor.

As used herein, the term "splint oligonucleotide" refers to a nucleotide sequence that functions to hybridize to an oligonucleotide of a labeled protein aggregate. In some embodiments, the splint olignucleotide comprises a region complementary to a left oligonucleotide, and a region complementary to a right oligonucleotide, such that the hybridization of the left oligonucleotide and the right oligonucleotide to the splint oligonucleotide can result in a substrate suitable for ligation. In some embodiments, the splint oligonucleotide can hybridize to an oligonucleotide, thus allowing for an extension reaction or a digestion reaction, as discussed for example in published US Patent Application US20070026430.

As used herein, the term "label" refers to any of a variety of moieties that can identify a molecule and allow for its detection, examples including fluorophores, chemiluminescent molecules, radioactivity, quantum dots, etc.

As used herein, the term "breaking-up" refers to a step in which a protein aggregate is separated into a number of smaller protein aggregates, as can be achieved for example by sonication or heat.

PLA for Protein Aggregate Detection

The present teachings provide a method of detecting protein aggregates. The method takes advantage of the close proximity of self-assembled molecules in aggregated prion particles (or other naturally occurring homo-multimeric protein complexes) An illustrative embodiment of the reagents used in one method according to the present teachings is depicted in FIG. 1. Here, a soluble precursor molecule (1), yeast Sup35 molecule for example, is labeled with left oligonucleotides (2) to form a first labeled precursor (3), and a second soluble precursor molecule (4), also for example another molecule of yeast Sup35,is labeled with right oligonucleotides (5), to form a second labeled precursor (6). Each of the yeast Sup35 precursors in FIG. 1 comprise an N-terminal (8) and a C-terminal (9). The oligonucleotide labels (2 and 5) are shown attached to the two C-terminals (9, 9). A particular left oligonucleotide (21) and right oligonucleotide (20) is also shown, the relevance of which will become increasingly apparent as the figures proceed.

Figure 2:
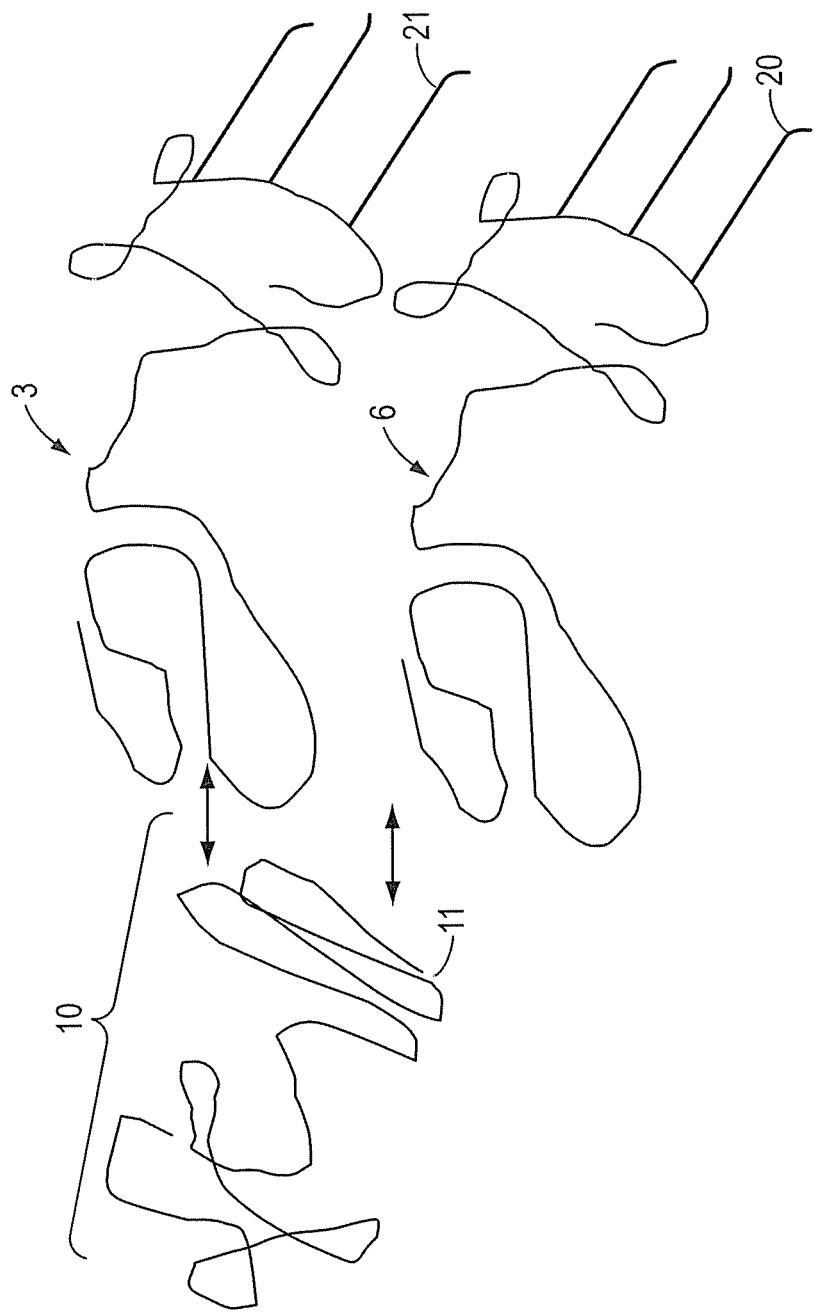
FIG. 2 depicts some embodiments of the present teachings for detecting a protein aggregate.

FIG. 2 depicts a reaction mixture comprising an protein aggregate (for example aggregated Sup35), here focusing on a single protein monomer in the protein aggregate (10), comprising a prion domain N-terminus (11). The reaction mixture further comprises the first labeled precursor (3) and the second labeled precursor (6), each bearing their respective oligonucleotides (21 and 20).

Figure 3:
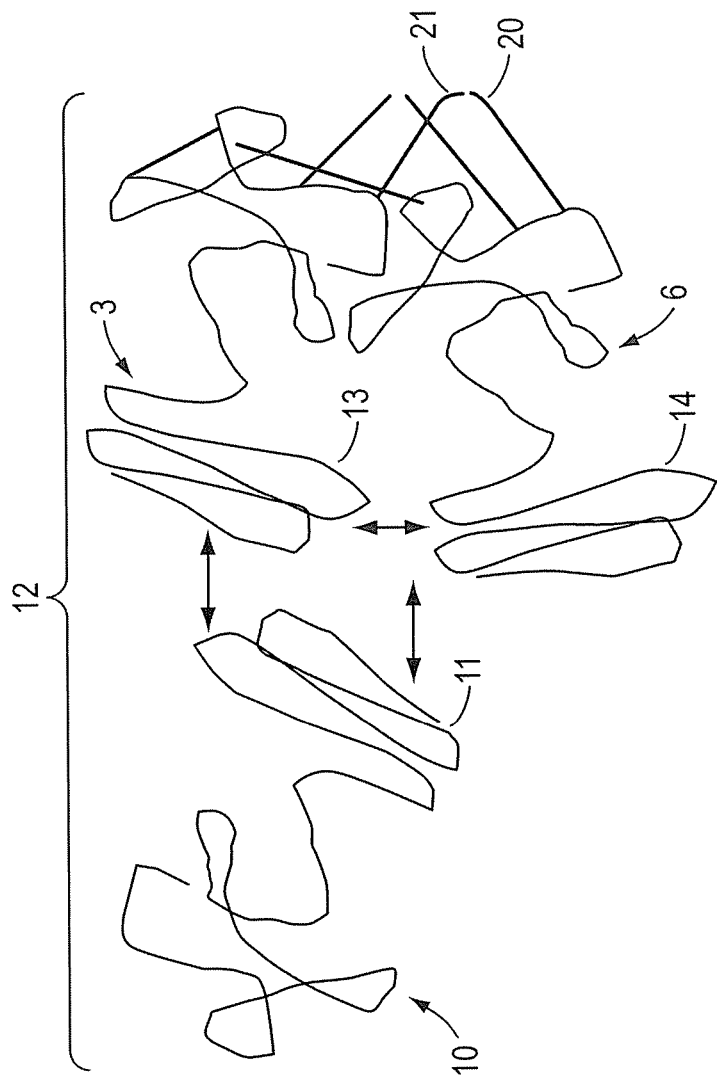
FIG. 3 depicts some embodiments of the present teachings for detecting a protein aggregate.

FIG. 3 depicts the result of the folding of the first labeled precursor (3) and the second labeled precursor (6) with the prion domain N-terminus (11) of the protein aggregate (10), resulting in the labeled precursors' incorporation into the protein aggregate to form a labeled protein aggregate (12). The labeled protein aggregate (12) comprises a misfolded N-terminus (13) of the first labeled precursor (3), and a misfolded N-terminus (14) of the second labeled precursor (6). Left oligonucleotide (21) and the right oligonucleotide (20) are now proximal to each other due to the incorporation of their corresponding precursors into the aggregate, and are now positioned to allow for their interaction.

Figure 4:
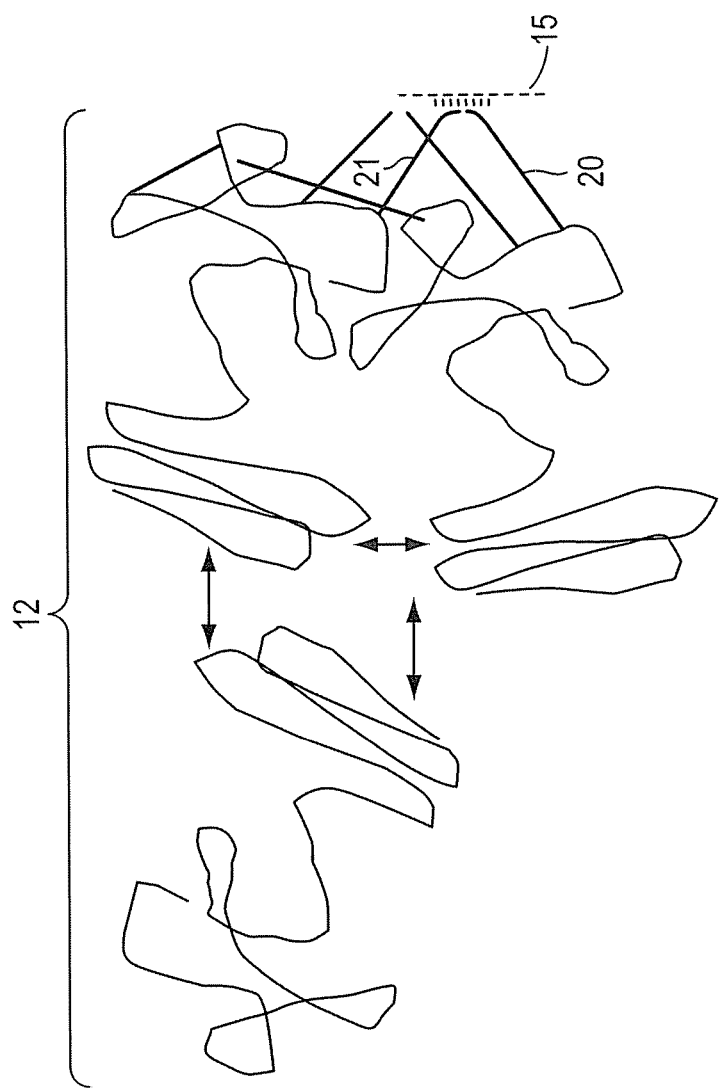
FIG. 4 depicts some embodiments of the present teachings for detecting a protein aggregate.

In FIG. 4, a splint oligonucleotide (dashed, 15) is shown hybridized to the left oligonucleotide (21) and the right oligonucleotide (22) of the labeled protein aggregate (12), thus providing a substrate suitable for a ligation reaction.

Figure 5:
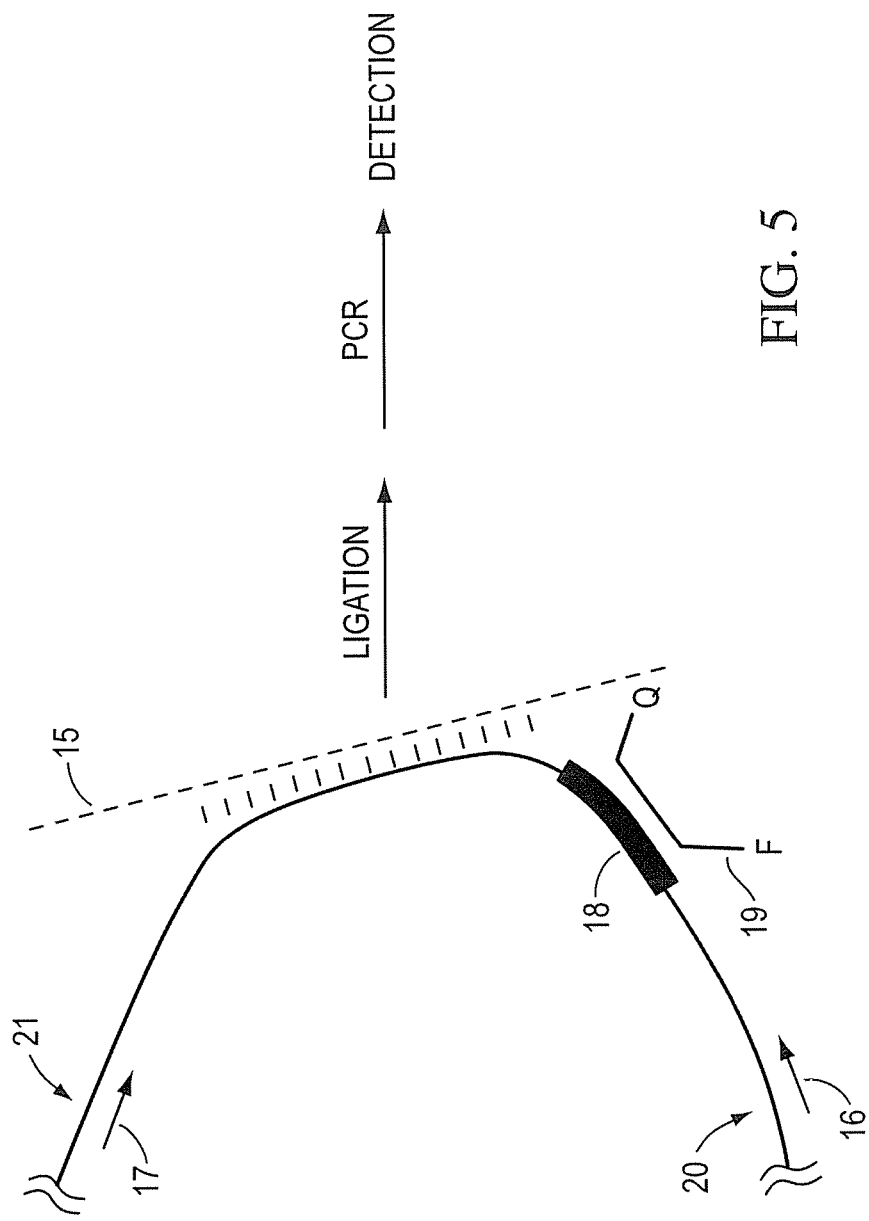
FIG. 5 depicts some embodiments of the present teachings for detecting a protein aggregate.
Figure 6:
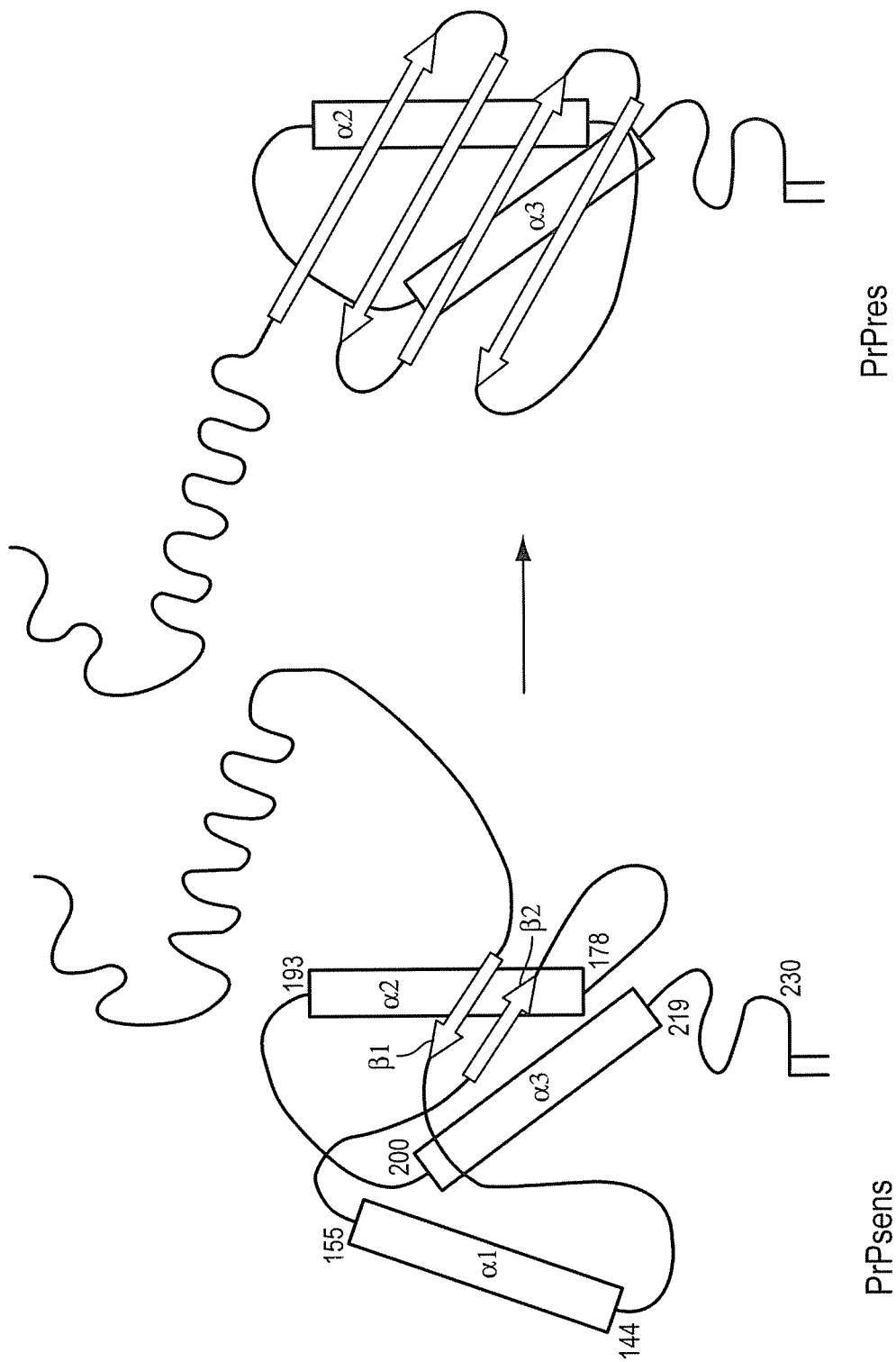
FIG. 6 depicts an illustrative analyte, BSE, which the present teachings can be employed to detect.

In FIG. 5, a close-up depiction of the splint oligonucleotide (15) hybridized to the left oligonucleotide (21) and right oligonucleotide (20) is shown. The oligonucleotides can comprise sequence information against which PCR primers (16 and 17) can be designed. As a result of ligation, a PCR amplifiable molecule (a ligation product) is formed. That is, extension of a primer copies the ligation product, and is not interrupted by the gap between primer sites that was present prior to the aggregation-induced proximity of the left and right oligonucleotides. Thus, a ligation followed by PCR approach allows for the detection of the formation of the labeled protein aggregate, and hence for the detection of the protein aggregate in the sample (10, in FIG. 2). As shown in FIG. 5, the left oligonucleotide (21) and right oligonucleotide (20) can be ligated and the resulting ligation product can be detected in a real-time PCR such as TaqMan®), wherein a 5' nuclease probe (a TaqMan probe, (19, comprising a fluorophore (F) and a quencher (Q))) is employed that queries sequence present in one or both of the oligonucleotide probes (for example, 18).

Thus, in some embodiments the present teachings provide for the elimination of the need for antibodies or other heterologous binders. In their place, the present teachings can elegantly take advantage of the self-assembly properties of these misfolded proteins.

In some embodiments, the present teachings can be applied in a variety of contexts by derivatizing the corresponding precursor with an appropriate oligonucleotide. Such derivitized precursors can then be used to detect their aggregated counterparts in biological samples. For example, in some embodiments the present teachings can be employed for the detection of the beta amyloid protein, the huntingtin protein, alpha-synuclein, and/or BSE.

Thus, in some embodiments the present teachings provide a method of detecting a protein aggregate in a sample of interest comprising; providing a first precursor molecule and a second precursor molecule, wherein the first precursor molecule comprises a first oligonucleotide, and wherein the second precursor molecule comprises a second oligonucleotide; contacting a sample suspected of containing the protein aggregate with the first precursor molecule and the second precursor molecule;

incorporating the first precursor molecule and the second precursor molecule into the protein aggregate, if present, to form a labeled protein aggregate; interacting the first oligonucleotide of the first precursor molecule with the second oligonucleotide of the second precursor molecule, to form an interaction composition; and, measuring the interaction composition to detect the presence of the protein aggregate in the sample of interest.

In some embodiments, the interacting comprises hybridizing the first oligonucleotide and the second oligonucleotide to a splint oligonucleotide and ligating the first oligonuceotide to the second oligonucleotide to form a ligation product. In some embodiments, the first precursor molecule and the second precursor molecule are Sup35.In some embodiments, the first precursor molecule and the second precursor molecule are beta amyloid protein. In some embodiments, the first precursor molecule and the second precursor molecule are huntingtin. In some embodiments, the first precursor molecule and the second precursor molecule are alpha-synuclein. In some embodiments, the first precursor molecule and the second precursor molecule are BSE. In some embodiments, the detecting comprises amplifying the ligation product in a PCR. In some embodiments, the PCR is a real-time PCR.

The present teachings also provide accompanying reaction compositions. For example, in some embodiments the present teachings provide a reaction composition comprising; a protein aggregate, a first precursor molecule, and a second precursor molecule, wherein the first precursor molecule comprises a first oligonucleotide, and wherein the second precursor molecule comprises a second oligonucleotide.

In some embodiments, the first precursor molecule and the second precursor molecule are Sup35.In some embodiments, the first precursor molecule and the second precursor molecule are beta amyloid protein. In some embodiments, the first precursor molecule and the second precursor molecule are huntingtin. In some embodiments, the first precursor molecule and the second precursor molecule are alpha-synuclein. In some embodiments, the first precursor molecule and the second precursor molecule are BSE.

In some embodiments, a single labeled precursor can be employed. For example, a collection of precursors bearing an oligonucleotide can be incorporated into a labeled protein aggregate. After washing unincorporated labeled precursors away, the remaining incorporated precursors, and the oligonucleotides attached thereto, can be detected. Such detection can comprise, for example, a PCR amplification employing primers designed to a first region of the oligonucleotide and a second region of the oligonucleotide.

Thus, in some embodiments the present teachings provide a method of detecting a protein aggregate in a sample of interest comprising; providing a precursor molecule, wherein the precursor molecule comprises an oligonucleotide; contacting a sample suspected of containing the protein aggregate with the precursor molecule; incorporating the first precursor molecule into the protein aggregate, if present, to form a labeled aggregate protein; removing unincorporated precursor molecules; and, measuring the labeled protein aggregate to detect the presence of the protein aggregate in the sample of interest.

In some embodiments, the detecting occurs after a breaking-up. In some embodiments,the detecting occurs in the absence of a breaking-up. In some embodiments, the detecting comprises amplifying the oligonucleotide. In some embodiments, the amplifying comprises PCR. In some embodiments, the PCR is a real-time PCR. In some embodiments, the precursor molecule is Sup35 In some embodiments, the precursor molecule is beta amyloid protein. In some embodiments, the precursor molecule is huntingtin. In some embodiments, the precursor molecule is alpha-synuclein. In some embodiments, the precursor molecule is BSE.

The present teachings also provide accompanying reaction compositions. For example, in some embodiments the present teachings provide a reaction composition comprising; a protein aggregate and a precursor molecule, wherein the precursor molecule comprises a label, wherein the label is an oligonucleotide.

In some embodiments, the precursor molecule is Sup35.In some embodiments, the precursor molecule is beta amyloid protein. In some embodiments, the precursor molecule is huntingtin. In some embodiments, the precursor molecule is alpha-synuclein. In some embodiments, precursor molecule is BSE.

A set of illustrative experiments are now described. Analogous experiments are readily applicable by one of ordinary skill in the art of molecular biology in light of the present teachings. For example, the present teachings can readily be applied for the detection of Bovine Spongiform Encephalopathy (BSE) (FIG. 5).

A model system based on the yeast Sup35 prion has been used to demonstrate the feasibility of this approach. Sup35 contains five cysteines in the carboxyl region—none of which are involved in disulfide bridges (see FIGS. 1-2, as well as Chembiochem. May 2006;7(5):757-65,and Nat Cell Biol. November 2005;7(11):1039-44). Since the amino terminus region is involved in misfolding, the cysteine-containing regions can be available to participate in an interaction, such as that which occurs in the proximity ligation assay (PLA). These cysteines offer a convenient means to attach labels to the Sup35 protein, for example thio-derivatized oligonucleotides. One aliquot of Sup35 is conjugated with the left oligonucleotide, and the other aliquot is conjugated with the right oligonucleotide. Mixing these two reagents together is predicted to give little or no background signal in a PLA experiment. However, in the presence of the prion form of Sup35,the conjugated proteins would be predicted to become aggregated and therefore proximal (FIGS. 3-4). After a ligation step, the complex can provide a positive real-time PCR signal. Of course, real-time PCR is not the only detection format possible for measuring self-assembly aggregates. For example, flourescence tagged monomers can be used for a proximal-based fluorescence increase or decrease. In another example, PCR amplified oligonucleotides can contain zipcode sequences, and the resulting amplicons hybridized to a microarray for an array-based readout. Any of a variety of other detection methods are readily available to one of ordinary skill in the art of molecular biology and can be employed following routine experimentation.

Cloning of Yeast SUP35 for Bacterial Expression:

The full-length open-reading frame for the wild-type SUP35 gene was amplified in two rounds of PCR from wild-type yeast cell lysate prepared by boiling cells in water. The first PCR used the primers SUP35_F1(SEQ ID NO: 1) and SUP35_R1 (SEQ ID NO: 2) in a 50 uL reaction containing 10% cell lysate, 1× PCR buffer (Applied Biosystems), 3 mM $MgCl_2$, 2 mM dNTPs, 2 uM primer F1 and R1 and 12.5 units AmpliTaq Gold DNA polymerase.

SEQ ID NO: 1    CTTCATCGACTTGCTCGGAATAACAT

SEQ ID NO: 2    GGAAGGGTTATGATGAAAACGTGATTG

The following PCR conditions were used: 95° C. 10 min, and 35 cycles of 95° C., 15 sec, 50° C., 30 sec, 68° C., 2 min. 1 uL of PCR product was re-amplified in a second 50 ul PCR as above except that the following primers were used: Sup35_F2 (SEQ ID NO: 3) and Sup35_R2 (SEQ ID NO: 4).

SEQ ID NO: 3    GCGGATCCATGTCGGATTCAAACCAAGGCAAC

SEQ ID NO: 4    GCCTCGAGCTCGGCAATTTTAACAATTTTACCA

Purified PCR product was digested with BamHI and XhoI (New England Biolabs) according to the manufacturer's instructions, and ligated with T4 DNA ligase (New England Biolabs) into the pET30-a vector (Novagen), which was similarly digested with BamHI and XhoI to form the construct designated pET30-Sup35-1.

Bacterial Expression of Recombinant SUP35:

BL21 (DE3) pLysS cells were transformed with expression construct pET30-Sup35-1.Freshly inoculated cultures (1-4L) containing 30 ug/ml kanamycin were grown with shaking to an $O.D._{600}=1.0$.IPTG was then added to a final concentration of 0.5-1 mM, and incubation continued for an additional 2-4 hrs at 37° C. with shaking. Cells were pelleted and frozen at −20° C. until use for protein purification.

Recombinant SUP35 Protein Purification:

Cells were resuspended in 5 ml (per gram of cell pellet) BugBuster reagent (Novagen), supplemented with 25U (1 ul) of Benzonase nuclease (Novagen) per 5 ml of reagent. The lysate was incubated on a rocking platform for 20 min at room temperature. Insoluble material was removed by pelleting at 16000×g for 20 min at 4° C. The supernatant (soluble protein fraction) was added to 1 ml of pelleted NiNTA resin (Novagen) and incubated at 4° C. for 1 hr with rocking. The resin was then loaded into a column and washed once with 10 ml of 1× binding buffer (300 mM NaCl, 50 mM sodium phosphate buffer, pH8.0) containing 20 mM imidazole and once with 10 ml of 1× binding buffer containing 50 mM imidazole. The bound protein was eluted with 1× binding buffer containing 250 mM imidazole. One 1.5 ml fraction and three 1 ml fractions were collected. The majority of bound protein is typically eluted in the first two fractions. Eluted protein was dialized into 0.1× PBS, pH7.4 containing 5 mM EDTA and stored at 4° C. It was found that the recombinant protein formed fiberous aggregates over time at 4° C. in the presence of 1× PBS, pH7.4 and certain detergents such as 0.1% SDS and 0.01% Triton-X100.However, it was found that no fiberous aggregates are formed over time when the protein is stored at 4° C. in 0.1× PBS, pH7.4 with 5 mM EDTA. Additional procedures for minimizing aggregate formation can be found in the art, for example Arora et al., Febs Letters 564 (2004) 121-125,and Balbirnie et L., PNAS, (2001) 98:5:2375-2380.

Preparation of SUP35 PLA Probes:

Biotinylation of Sup35:

Recombinant SUP35 was biotinylated by adding 0.53 uL of 2 mg/ml $NHS-PEO_4$-Biotin reagent (Pierce) to 100 uL of SUP35 (100 ug/mL) protein, and incubating at room temperature for 30 min. The reaction mixture was then dialyzed overnight in 0.1× PBS, pH7.4 containing 5 mM EDTA at 4° C.

Proximity Probe Conjugation:

Biotinylated SUP35 was diluted to 200 nM in buffer C (1× PBS, pH7.4, 5 nM EDTA, 0.1% BSA). 5 uL of biotinylated SUP35 was combined with either 5 uL of reagent A (200 nM streptavidin-linked oligo A) or 5 uL of reagent B (200 nM streptavidin-linked oligo B) and incubated at room temperature for 1 hour. Each proximity probe was diluted to 1 nM in buffer D (1× PBS, pH7.4, 1% BSA, 16 ug/ml polyA, 1 mM biotin) and incubated at room temperature for 20 minutes. Probes were stored at 4° C.

EXAMPLE 1

Detection of SUP35 Prion Protein in the Prion-Positive Yeast Strain 5V-H19 psi+

Preparation of Yeast Cell Lysates:

Wild-type Saccharomyces cerevisiae (ATCC #9763) and the SUP35 prion-positive strain 5V-H19 psi+ (ATCC #201250) were streaked on separate YEPD plates, and grown at 30° C. for 48 hours. 60 mg of cells were scraped off of each plate, and frozen overnight at −20° C. Cells were resuspended in 300 uL of lysis buffer (Y-PER [Pierce #78991] supplemented with 1× protease inhibitor cocktail [Calbiochem # 539131] and 5 mM DTT and incubated on a shaker at room temperature for 10 minutes. Cellular debris was removed by centrifugation at 500×g for 10 minutes at 4° C. The supernatant (soluble fraction) from each sample was used for prion detection.

Prior to PLA, lysates were diluted 1:100 by adding 1 uL of soluble yeast lysate into 99 uL buffer D or buffer D+5 mM $MgCl_2$. Serial dilutions of 1:10 were subsequently prepared for PLA analysis.

Figure 7:
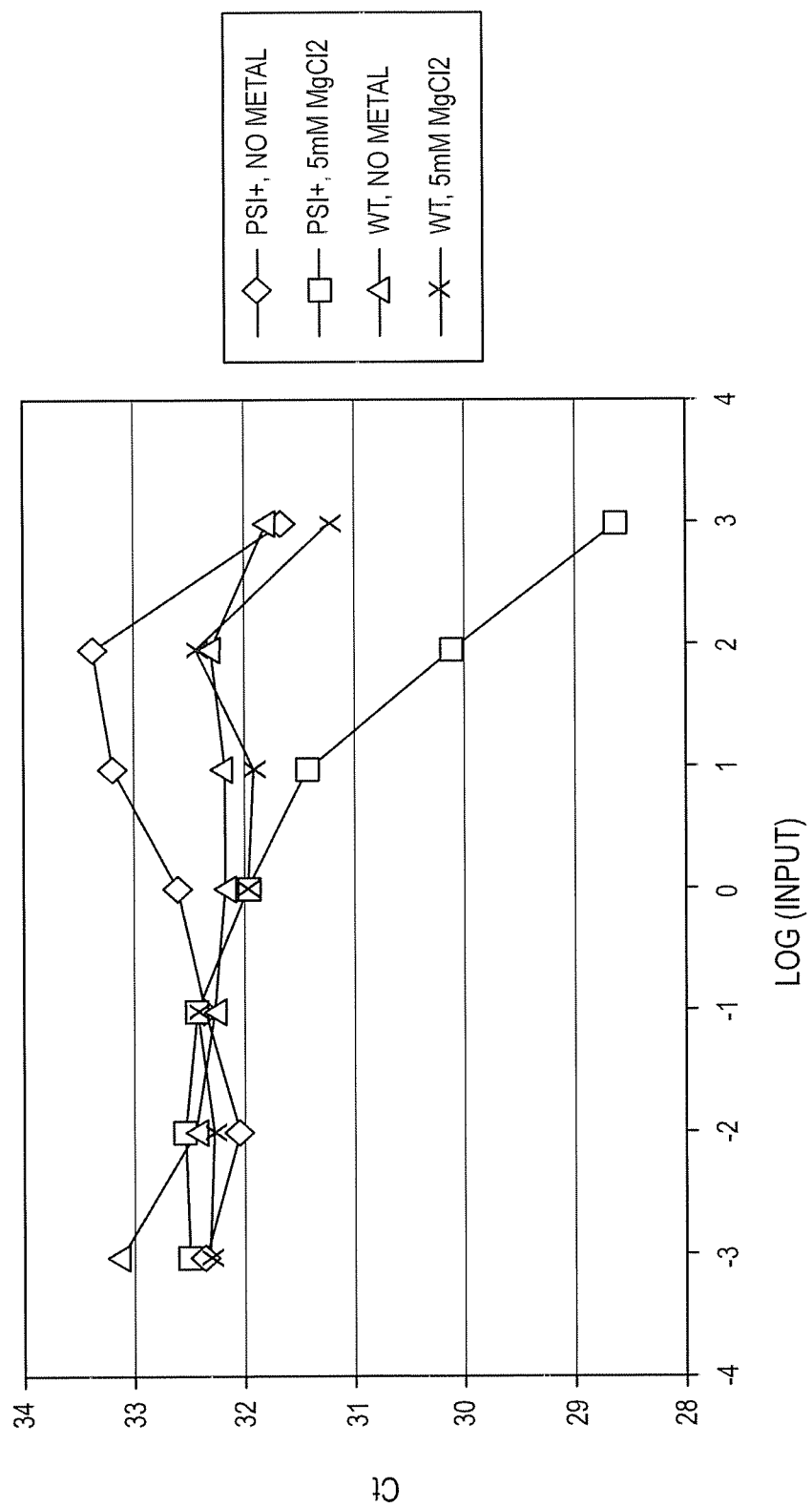
FIG. 7 depicts some illustrative data according to some embodiments of the present teachings.

PLA Procedure for Prion Detection:

PLA was carried out by first adding 1 uL of each diluted yeast lysate sample to 4 uL SUP35 probe mix (A and B), which was prepared in buffer D (for a final probe concentration of 30 pM final concentration for each probe), and incubated at 37° C. for 5 hours. Buffer D contained 1× PBS, pH7.4, 1% BSA, 16 ug/ml polyA, 1 mM biotin. 45 uL of ligation/PCR mix containing 50 mM KCl, 20 mM Tris,pH8.3, 2.5 mM $MgCl_2$, 200 uM dNTPs, 80 uM ATP, 400 nM connector oligo, 500 nM forward primer, 500 nM reverse primer, 200 nM probe, 0.4 units T4 DNA ligase (New England Biolabs), 1.5 units Platinum Taq (Invitrogen), and passive reference ROX (Applied Biosystems) was then added and the mixture was incubated at 37° C. for 5 minutes before being cooled to 4° C. for 5 minutes. 10 uL aliquots of the proximity ligation product were transferred to individual wells of a 384-well PCR plate and real-time quantitative PCR was performed according to the following cycling parameters: 95° C. 2 min, 40 cycles of 95° C. 15 sec, 60° C. 60 sec, with a 7900HT instrument (Applied Biosystems). Results are shown in FIG. 7. Average $C_T$ values for diluted yeast lysate samples are plotted in relation to the log of the input dilution. It is noteworthy that the assay provides a positive, input concentration-dependent result with the prion-containing cell lysate as reflected by lower $C_T$ values when higher amounts of prion-positive lysate are assayed, but not with lysates from the wild-type strain. It is also noteworthy that the assay comprises the addition of $MgCl_2$ to at least 1 mM for efficient prion detection.

EXAMPLE 2

PLA with PEG Precipitated Fractions from Yeast Lysates

PEG-3350 has been shown previously to partition self-aggregated prion protein complexes from protein monomers by precipitating the aggregates and leaving the monomers in solution. See Lee et al., WO 01/38354. This property was used to partition the SUP35 prion form from soluble monomers in yeast cell lysates. In this example, liquid cultures of yeast were prepared by inoculating one colony into 10 mL of YEPD broth and incubating on a shaker at room temperature until cultures reached an $OD_{60}=1.0$ for the wild-type strain or $OD_{600}=0.4$ for the PSI+ strain. The cultures were centrifuged at 4,000 rpm for 10 min, the media was decanted the pellets were frozen at −20° C. overnight. Cell pellets were resuspended in Y-PER lysis buffer to a final concentration (w/v) of 200 ug/ul. Cell suspensions were incubated on a shaker at room temperature for 10 minutes and then centrifuged at 500×g for 10 minutes at 4° C. to pellet insoluble material. The supernatant (soluble fraction) was held on ice until use. 32 mg of solid PEG-3350 was added to 250 uL of WT and PSI+ soluble yeast lysate over 15 minutes on ice, shaking every minute. This step was followed by an additional incubation on ice for 30 minutes, shaking every minute. The samples were then centrifuged at 5,000×g for 5 minutes at 4° C. The resulting supernatant was discarded and the pellet was resuspended in 20 uL of lysis buffer (Y-PER).

Prior to PLA, lysates were diluted 1:100 by adding 1 uL soluble yeast lysate into 99 uL buffer D or buffer D+5 mM $MgCl_2$. Serial dilutions of 1:5 were subsequently prepared for PLA analysis.

Figure 8:
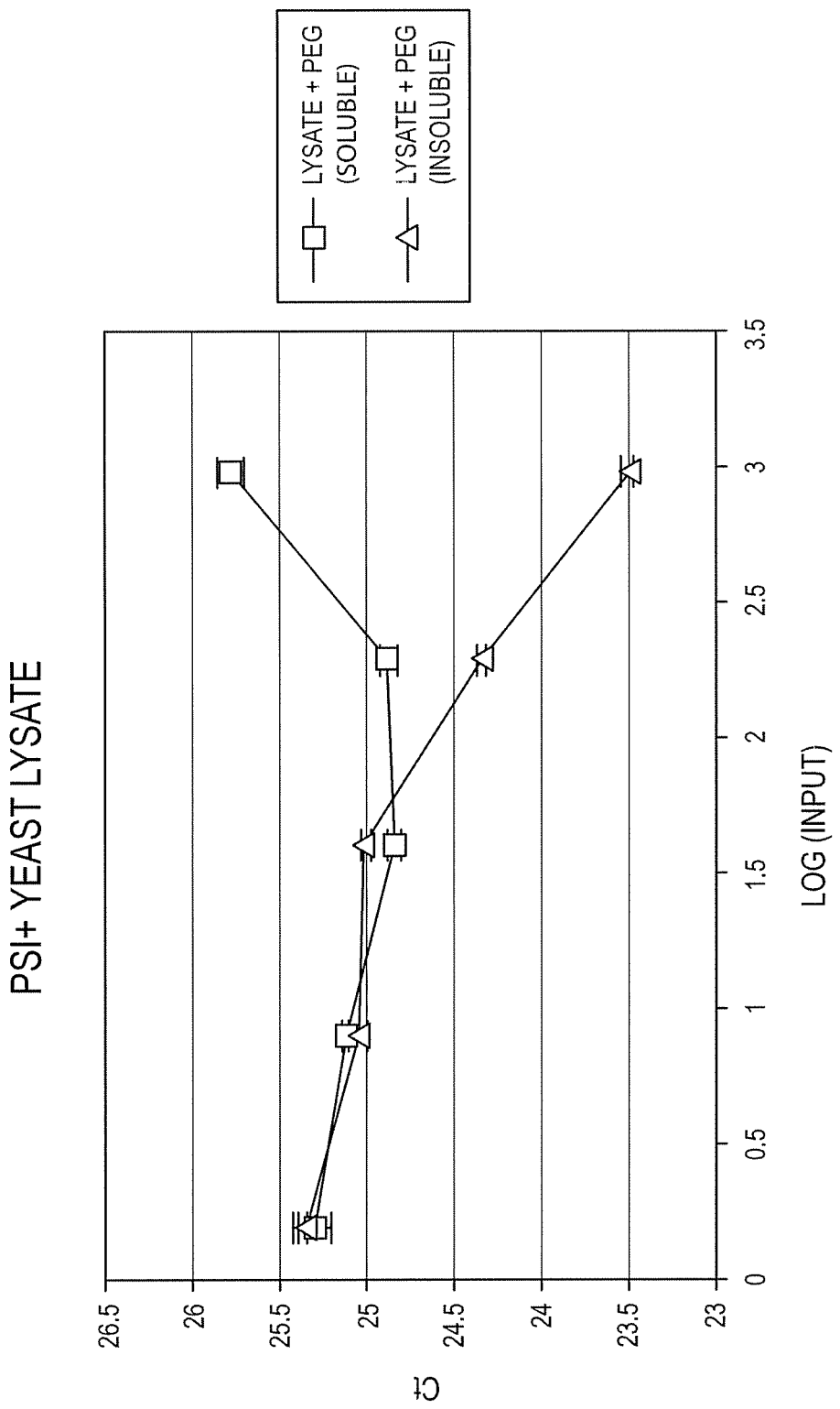
FIG. 8 depicts some illustrative data according to some embodiments of the present teachings.
Figure 9:
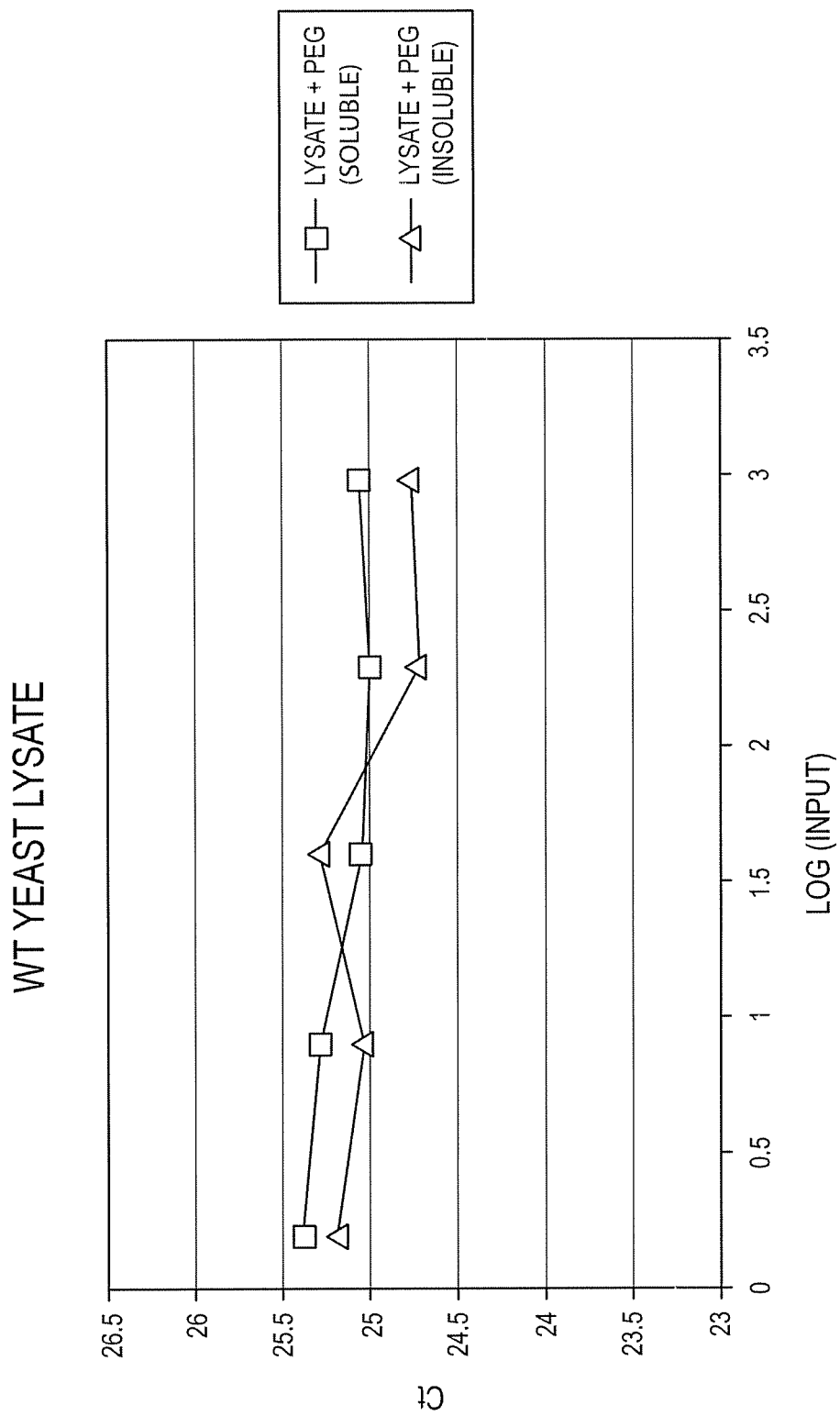
FIG. 9 depicts some illustrative data according to some embodiments of the present teachings.

In this example, PLA was carried out by first adding 1 uL of each diluted yeast lysate sample to 4 uL Sup35 probe mix (A and B), which was prepared in buffer D (for a final probe concentration of 30 pM final concentration for each probe), and incubated at 37° C. for 4 hours. 45 uL of ligation/PCR mix containing 1× Fast Universal Master Mix, 400 nM connector oligo, 80 uM ATP (Sigma), 0.4 T4 DNA ligase (New England Biolabs), 500 nM forward primer, 500 nM reverse primer, 200 nM probe was then added and the mixture was incubated at 37° C. for 5 minutes before being cooled to 4° C. for 5 minutes. 10 uL aliquots of the proximity ligation product were transferred to 384-well PCR plates and real-time quantitative PCR was performed according to the following cycling parameters: 95° C. 2 min, 40 cycles of 95° C. 15 sec, 60° C. 60 sec, with a 7900HT instrument (Applied Biosystems). Results are shown in FIGS. 8-9. Average $C_T$ values for diluted yeast lysate samples are plotted in relation to the log of the input dilution. It is noteworthy that the assay provides a positive, input concentration-dependent result with the PEG-3350 insoluble cell lysate fraction as reflected by lower $C_T$ values when higher amounts of prion-positive lysate are assayed, but not with PEG-3350 soluble cell lysate fraction. (FIG. 9). It is also noteworthy that the assay does not detect prion aggregates in either PEG-3350 soluble or insoluble fractions from wild-type yeast (FIG. 9).

Certain Exemplary Kits

The instant teachings also provide kits designed to expedite performing certain of the disclosed methods. Kits may serve to expedite the performance of certain disclosed methods by assembling two or more components required for carrying out the methods. In certain embodiments, kits contain components in pre-measured unit amounts to minimize the need for measurements by end-users. In some embodiments, kits include instructions for performing one or more of the disclosed methods. Preferably, the kit components are optimized to operate in conjunction with one another.

Thus, in some embodiments the present teachings provide a kit for detecting a protein aggregate in a sample of interest comprising; a first precursor molecule and a second precursor molecule, wherein the first precursor molecule comprises a first oligonucleotide, and wherein the second precursor molecule comprises a second oligonucleotide. In some embodiments, the kit further comprises a ligase. In some embodiments, the kit further comprises reagents for a PCR, wherein the reagents for the PCR comprise a first primer and a second primer, wherein the first primer corresponds to the first oligonucleotide of the first precursor molecule and wherein the second primer corresponds to the second oligonucleotide of the second precursor molecule.

In some embodiments, the present teachings provide a kit for detecting a protein aggregate in a sample of interest comprising; a precursor molecule, wherein the precursor molecule comprises an oligonucleotide. In some embodiments, the kit further comprises a polymerase. In some embodiments, the kit further comprises reagents for a PCR, wherein the reagents for the PCR comprise a first primer and a second primer, wherein the first primer corresponds to a first region of the oligonucleotide of the first precursor molecule and wherein the second primer corresponds to a second region of the oligonucleotide of the first precursor molecule.

Although the disclosed teachings have been described with reference to various applications, methods, and kits, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

We claim:

1. A method of detecting a protein aggregate in a sample of interest comprising:
   providing a first soluble precursor molecule and a second soluble precursor molecule, wherein the first precursor molecule is attached to a first oligonucleotide, and wherein the second precursor molecule is attached to a second oligonucleotide, wherein the first soluble precursor molecule and the second soluble precursor molecule are capable of aggregating;
   contacting a sample suspected of containing the protein aggregate with the first soluble precursor molecule and the second soluble precursor molecule;
   aggregating the first soluble precursor molecule, and the second soluble precursor molecules and the protein aggregate, if present in the sample, together to form an oligonucleotide-labeled protein aggregate, wherein the first and second precursor molecules are incorporated into the labeled protein aggregate;
   interacting the first oligonucleotide of the first precursor molecule with the second oligonucleotide of the second precursor molecule, to form an interaction composition; and,
   detecting the interaction composition to detect the presence of the protein aggregate in the sample of interest; wherein the interacting comprises hybridizing the first oligonucleotide and the second oligonucleotide to a splint oligonucleotide and ligating the first oligonucleotide to the second oligonucleotide to form a ligation product.

2. The method according to claim 1 wherein the first precursor molecule and the second precursor molecule are Sup35.

3. The method according to claim 1 wherein the detecting comprises amplifying the ligation product in a PCR.

4. The method according to claim 3 wherein the PCR is a real-time PCR.

* * * * *

UNITED STATES PATENT AND TRADEMARK OFFICE
CERTIFICATE OF CORRECTION

| | | |
|---|---|---|
| PATENT NO. | : 8,535,878 B2 | Page 1 of 1 |
| APPLICATION NO. | : 11/743517 | |
| DATED | : September 17, 2013 | |
| INVENTOR(S) | : Ruff et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 296 days.

Signed and Sealed this
Seventh Day of April, 2015

Michelle K. Lee
*Director of the United States Patent and Trademark Office*